US010894004B2

(12) United States Patent
Constantine et al.

(10) Patent No.: US 10,894,004 B2
(45) Date of Patent: Jan. 19, 2021

(54) COMPOSITION

(71) Applicant: COSMETIC WARRIORS LIMITED, Poole (GB)

(72) Inventors: Mark Constantine, Poole (GB); Margaret Joan Constantine, Poole (GB); Rowena Jacqueline Bird, Christchurch (GB); Helen Elizabeth Ambrosen, Poole (GB)

(73) Assignee: COSMETIC WARRIORS LIMITED, Poole (GB)

( * ) Notice: Subject to any disclaimer, the term of this patent is extended or adjusted under 35 U.S.C. 154(b) by 0 days.

(21) Appl. No.: 15/777,637

(22) PCT Filed: Dec. 1, 2016

(86) PCT No.: PCT/GB2016/053770
§ 371 (c)(1),
(2) Date: May 18, 2018

(87) PCT Pub. No.: WO2017/093733
PCT Pub. Date: Jun. 8, 2017

(65) Prior Publication Data
US 2018/0344585 A1    Dec. 6, 2018

(30) Foreign Application Priority Data
Dec. 3, 2015 (GB) .................................. 1521384.6

(51) Int. Cl.
| *A61Q 11/00* | (2006.01) |
| *A61K 8/02* | (2006.01) |
| *A61K 8/20* | (2006.01) |
| *A61K 8/34* | (2006.01) |
| *A61K 8/365* | (2006.01) |
| *A61K 8/362* | (2006.01) |
| *A61K 8/60* | (2006.01) |
| *A61K 8/24* | (2006.01) |
| *A61K 9/46* | (2006.01) |
| *A61K 9/28* | (2006.01) |
| *A61K 9/00* | (2006.01) |

(52) U.S. Cl.
CPC .............. *A61K 8/0216* (2013.01); *A61K 8/20* (2013.01); *A61K 8/24* (2013.01); *A61K 8/345* (2013.01); *A61K 8/362* (2013.01); *A61K 8/365* (2013.01); *A61K 8/60* (2013.01); *A61Q 11/00* (2013.01); *A61K 9/0007* (2013.01); *A61K 9/0063* (2013.01); *A61K 9/2813* (2013.01); *A61K 2800/222* (2013.01)

(58) Field of Classification Search
CPC ........ A61K 8/0216; A61K 8/24; A61K 8/362; A61K 8/365; A61K 8/345; A61K 8/20; A61K 2800/222; A61Q 11/00
See application file for complete search history.

(56) References Cited

U.S. PATENT DOCUMENTS

| 3,629,468 | A |   | 12/1971 | Andersen |           |
|-----------|---|---|---------|----------|-----------|
| 4,127,645 | A | * | 11/1978 | Witzel   | A23G 3/36 |
|           |   |   |         |          | 424/401   |
| 5,057,305 | A |   | 10/1991 | Aberg    |           |
| 5,804,165 | A |   | 9/1998  | Arnold   |           |
| 5,817,294 | A |   | 10/1998 | Arnold   |           |
| 6,086,854 | A |   | 7/2000  | Arnold   |           |
| 6,177,097 | B1 |  | 1/2001  | Hanke    |           |
| 6,300,295 | B1 |  | 10/2001 | Knollmann et al. | |
| 8,192,724 | B2 |  | 6/2012  | Rau      |           |
| 9,185,924 | B2 | * | 11/2015 | Elejalde | A23G 4/10 |
| 2004/0247532 | A1 | | 12/2004 | Pinol et al. | |
| 2006/0057078 | A1 | | 3/2006  | Rau      |           |
| 2007/0183984 | A1 | | 8/2007  | Haas et al. | |
| 2014/0227202 | A1 | * | 8/2014 | Pilgaonkar | A61K 8/0216 |
|           |   |   |         |          | 424/52    |
| 2015/0272873 | A1 | | 10/2015 | Boschetti et al. | |

FOREIGN PATENT DOCUMENTS

| CN | 102551169 A | 7/2012 |
| EP | 1057472 A1 | 12/2000 |
| EP | 2189154 A1 | 5/2010 |
| JP | S50-033691 A | 3/1975 |
| JP | H02-504030 A | 11/1990 |
| JP | H09-188610 A | 7/1997 |
| JP | H10-236935 A | 9/1998 |
| JP | H10-511093 A | 10/1998 |
| JP | 2000-501422 A | 2/2000 |
| JP | 2002-138026 A | 5/2002 |
| JP | 2002-308747 A | 10/2002 |
| JP | 2004-210721 A | 7/2004 |

(Continued)

OTHER PUBLICATIONS

International Search Report and Written Opinion for PCT/GB2016/053770, dated Feb. 21, 2017.
Search Report for British Patent Application No. 1521384.6, dated Oct. 20, 2016.
2.9.8. Resistance to Crushing of Tablets, European Pharmacopoeia 6.0 (2008).
Office Action for Japanese Patent Application No. 2018-526532, dated Sep. 28, 2020.
Search Report for Japanese Patent Application No. 2018-526532, dated Jul. 29, 2020.

*Primary Examiner* — Lezah Roberts

(74) *Attorney, Agent, or Firm* — Merchant & Gould P.C.

(57) ABSTRACT

A dental product in the form of a solid includes a mineral source. The mineral source includes a source or sources of calcium ions, phosphate ions or both calcium ions and phosphate ions. The dental product also includes a salt of carbonic acid, an acidifying agent and xylitol. The acidifying agent includes at least citric acid and malic acid, wherein the citric acid and malic acid are present in a weight ratio of from 4:1 to 1:1.

27 Claims, No Drawings

(56) References Cited

FOREIGN PATENT DOCUMENTS

| | | |
|---|---|---|
| JP | 2007-501273 A | 1/2007 |
| WO | 88/10110 A1 | 12/1988 |
| WO | 96/19194 A1 | 6/1996 |
| WO | 99/27901 A1 | 6/1999 |
| WO | 00/47181 A1 | 8/2000 |
| WO | 2004/100817 A2 | 11/2004 |
| WO | 2013/072932 A2 | 5/2013 |

* cited by examiner

COMPOSITION

This application is a National Stage of PCT/GB2016/053770, filed 1 Dec. 2016, which claims benefit of British Patent Application No. 1521384.6, filed 3 Dec. 2015, which applications are incorporated herein by reference. To the extent appropriate, a claim of priority is made to each of the above disclosed applications.

FIELD OF THE INVENTION

The present invention relates to a dental product, a process for producing said dental product, and a method for using the dental product.

BACKGROUND TO THE INVENTION

Over the course of the twentieth century the rapid transformation in both general health and oral health has continued unabated. However, millions of people worldwide have been deprived of the benefits afforded by socioeconomic development and scientific advances in industrialised nations, which has resulted in improved health outcomes and quality of life. A better understanding of the causes and ramifications of human dietary trends and poor oral care has led to a significant change in the way oral diseases are treated, shifting from a remedial or curative approach to oral care, to a largely preventative strategy.

It is well documented that regular preventative care reduces the incidence of both tooth decay and gum diseases, such as using a toothbrush, toothpaste, floss, mouthwash and the like. However, due to the increased consumption of refined foods and drinks high in sugar and acids worldwide, the incidence of oral diseases has increased as a direct result of a consumer's diet. One theory for this rise is due to the perceived inconvenience of a regular oral healthcare routine, such as brushing teeth after meals and regular interdental flossing. The use of convenient single-use or disposable oral hygiene products, such as treated mouth swabs, sugar-free chewing gum and solid mouthwash tablets, are seen as a way of supplementing a consumer's oral health care routine, improving oral health and reducing damage caused to a consumer's teeth as a result of acid erosion.

Solid mouthwash tablets are known in the art and often comprise a carbonate or bicarbonate source, an acidifying agent and flavourings. For example, U.S. Pat. No. 3,629,468 describes an effervescent mouthwash tablet comprising an acidic component and a salt capable of reacting with the acid component and evolving carbon dioxide in the presence of an aqueous medium, in addition to germicidal and breath freshening agents. U.S. Pat. No. 5,817,294 describes a non-aqueous effervescent dentifrice comprising a pharmaceutically acceptable carbon dioxide source, a non-aqueous water soluble acid and a carrier absorbent capable of absorbing plaque particles and other organic material. U.S. Pat. No. 8,192,724 describes a water soluble effervescent oral care tablet comprising a carbon dioxide source, an acid source, a tablet forming material and a flavouring agent sufficient to impart a favourable taste.

SUMMARY OF THE INVENTION

In a first aspect, there is provided a dental product in the form of a solid comprising (a) a mineral source, wherein the mineral source comprises a source or sources of calcium ions, phosphate ions or both calcium ions and phosphate ions; (b) a salt of carbonic acid; (iii) an acidifying agent; and (d) xylitol; wherein the acidifying agent comprises at least citric acid and malic acid, wherein the citric acid and malic acid are present in a weight ratio of from 4:1 to 1:1.

In a second aspect, there is provided a process for the production of a dental product as defined herein comprising the steps of: i) preparing a composition comprising (a) a mineral source, wherein the mineral source comprises a source or sources of calcium ions, phosphate ions or both calcium ions and phosphate ions; (b) a salt of carbonic acid; (c) an acidifying agent; and (d) xylitol; wherein the acidifying agent comprises at least citric acid and malic acid, wherein the citric acid and malic acid are present in a weight ratio of from 4:1 to 1:1, and ii) pressing the composition of step i) into the form of a tablet.

In a third aspect, there is provided a method for freshening and cleaning the mouth and breath, the method comprising
i) dissolving in the mouth a dental product as defined herein; and
ii) rinsing the dissolved product from the mouth.

For ease of reference, these and further aspects of the present invention are now discussed under appropriate section headings. However, the teachings under each section are not necessarily limited to each particular section.
Advantages We have found that an effervescent system was highly suited to the present invention as a way of effectively dissipating the active components of the composition, reducing or preventing the accumulation of plaque and organic particulates, whilst reducing malodorous breath such as that caused by volatile sulphur compounds and periodontal pathogens. The composition of the present invention may be placed directly on the tongue or in the mouth and allowed to dissolve and effervesce when mixed with saliva or a small amount of water. This allows for the effervescence to directly liberate organic particulates and reduce or prevent the accumulation of plaque from between the teeth and around the gum line.

Whilst it is well known that salts of carbonic acid will react with an acidifying agent in the presence of an aqueous medium to provide effervescence, it was surprisingly found that the rate of effervescence significantly affected the palatability of the composition. It was found that if the rate of effervescence was too vigorous or intense the taste and sensation of the composition was adversely affected, resulting in an unfavourable composition. However, if the vigour and intensity of effervescence was too low then the ability of the composition to reduce or prevent the accumulation of plaque and organic particulates and adequately disperse the active components was dramatically reduced, whilst adversely affecting the user experience.

The use of acidifying agents for oral care products needs to be carefully assessed to ensure that damage is not caused to the tooth enamel and dentin. Organic acids, such as citric acid and tartaric acid, have the potential to chelate metal ions in the saliva and the enamel, and create favourable conditions for dental plaque formation and bacterial proliferation. This results in a systematically damaging effect, giving rise to dental caries and other periodontal diseases.

The present inventors identified that the choice of organic acids is critical to achieve desirable effervescent properties when combined with sodium bicarbonate in the presence of an aqueous phase. For example, the present inventors found that the high rate of effervescence produced between sodium bicarbonate and citric acid, a typical system of the prior art, created an unpleasantly intense effervescent sensation in the oral cavity. In contrast the effervescence produced between sodium bicarbonate and tartaric acid was too low resulting in little or no effect on the accumulation of plaque and organic particulates and a poor user experience. The present inventors also identified that although sodium bicarbonate and malic acid produced a soothing effervescent effect; the ability of the effervescence to prevent the accumulation of plaque and organic particulates, whilst efficiently dispersing the active components, was deemed to be insufficient. It was surprisingly found that the optimum effervescence was obtained when sodium bicarbonate was combined with a mixture of citric acid and malic acid in a weight ratio of from 4:1 to 1:1. This specific combination of acids at a specific ratio of amounts resulted in sufficient effervescence to effectively reduce or prevent the accumulation of plaque and organic particulates from between the teeth and around the gum line, whilst creating a pleasant sensation within the oral cavity during use.

Whilst effectively reducing or preventing the accumulation of plaque and organic particulates is important to maintain a high degree of oral health, the remineralisation of the tooth enamel and dentin is imperative in order to help prevent dental caries, one of the most prevalent chronic diseases in industrialised nations. This remineralisation is facilitated in the present invention by the provision of a mineral source, wherein the mineral source comprises a source or sources of calcium ions and/or phosphate ions.

Furthermore it has been surprisingly found that the hardness of the composition has a direct effect on the user experience and on the potential of the composition to cause harm to the user during use. The use of salts of carbonic acid, acidifying agents and other components results in compositions of varying hardness. The composition of the present invention conferred a suitable hardness that means the composition does not readily fragment or fracture, and yet is not so hard as to cause harm to the user during use, for example by causing damage to the teeth. This hardness results in an overall positive user experience.

DETAILED DESCRIPTION

Composition

As discussed herein, in one aspect of the present invention, there is provided a dental product in the form of a solid comprising (a) a mineral source, wherein the mineral source comprises a source or sources of calcium ions, or phosphate ions or both calcium ions and phosphate ions; (b) a salt of carbonic acid; (c) an acidifying agent; and (d) xylitol; wherein the acidifying agent comprises at least citric acid and malic acid, wherein the citric acid and malic acid are present in a weight ratio of from 4:1 to 1:1.

Dental products of the present invention are compositions which can substantially sustain their physical shape when unsupported by external means, e.g. packaging etc. Thus, they are considered to be solid, solid like, in solid form or in solid-like form at room temperature. By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

As mentioned above, due to the solid form of the compositions of the present invention, external packaging is not required to maintain the shape of the composition.

Mineral Source

The dental product of the present invention comprises a mineral source. The mineral source according to the present invention comprises a source or sources of calcium ions, phosphate ions or both calcium ions and phosphate ions.

Demineralisation of the enamel and dentin occurs at pH levels typically lower than 5.5, as a result of localised plaque acids, whereby calcium and phosphate ions are leaved from the enamel and dentin, destabilising the core hydroxyapatite structure of the enamel and dentin, resulting in cavitation. Whilst the enamel and dentin are remineralised by calcium and phosphate ions present in saliva, this process is slow and often overcome by the damaging effect of excess acid in an individual's diet, favouring demineralisation of the dental substructures. By supplementing the available calcium and phosphate ions are amorphous that can be utilised to remineralise the tooth's enamel and dentin, the problem of demineralisation can be subdued.

In one aspect, the mineral source comprises a source or sources of calcium ions. In one aspect, the mineral source comprises a source or sources of phosphate ions. In one aspect, the mineral source comprises a source or sources of calcium ions and phosphate ions. In one aspect, the mineral source comprises a single source of both calcium ions and phosphate ions.

In one preferred aspect, the mineral source is selected from amorphous calcium phosphate, casein phosphor-peptides-amorphous calcium phosphate, monocalcium phosphate, dicalcium phosphate, tricalcium phosphate, octacalcium phosphate, calcium carbonate and mixtures thereof. It has been found that these compounds are able to dissociate calcium and phosphate ions in the saliva to varying degrees, which can then be used to remineralise the tooth's enamel and dentin.

In one preferred aspect, the mineral source is selected from amorphous calcium phosphate, casein phosphor-peptides-amorphous calcium phosphate, monocalcium phosphate, dicalcium phosphate, tricalcium phosphate, octacalcium phosphate, and mixtures thereof.

In one preferred aspect, the mineral source is at least dicalcium phosphate.

In some aspects, the mineral source (preferably dicalcium phosphate) is present in an amount of from 40 to 60 wt. % based on the weight of the dental product, such as in an amount of from 40 to 59 wt. % based on the weight of the dental product, such as in an amount of from 40 to 58 wt. % based on the weight of the dental product, such as in an amount of from 40 to 57 wt. % based on the weight of the dental product, such as in an amount of from 40 to 56 wt. % based on the weight of the dental product, such as in an amount of from 40 to 55 wt. % based on the weight of the dental product.

In some aspects, the mineral source (preferably dicalcium phosphate) is present in an amount of from 41 to 60 wt. % based on the weight of the dental product, such as in an amount of from 42 to 60 wt. % based on the weight of the dental product, such as in an amount of from 43 to 60 wt. % based on the weight of the dental product, such as in an amount of from 44 to 60 wt. % based on the weight of the dental product, such as in an amount of from 45 to 60 wt. % based on the weight of the dental product, such as in an amount of from 46 to 60 wt. % based on the weight of the dental product.

In one preferred aspect, the mineral source (preferably dicalcium phosphate) is present in an amount of from 45 to 55 wt. % based on the weight of the dental product.

Salt of Carbonic Acid

The dental product of the present invention comprises a salt of carbonic acid. In some aspects, the salt of carbonic acid is selected from alkali metal carbonates, and mixtures thereof. In some aspects, the salt of carbonic acid is selected from sodium bicarbonate, sodium carbonate, and mixtures thereof. In some aspects, the salt of carbonic acid is at least sodium bicarbonate. In some aspects, the salt of carbonic acid is sodium bicarbonate. In some aspects, the salt of carbonic acid is at least sodium carbonate.

Without being bound by theory, salts of carbonic acid, such as sodium bicarbonate, act as buffering agents when placed in to the oral cavity, effectively neutralising volatile sulphur compounds and other malodorous compounds, and promoting a clean and fresh oral environment. Furthermore salts of carbonic acid possess antimicrobial properties and are soothing to the oral mucosa, improving overall health, condition and freshness of the oral cavity.

The preferred salts of carbonic acid are alkali metal carbonates, more preferably sodium bicarbonate. Whilst sodium bicarbonate is known for its beneficial oral health properties, it also has the ability to neutralise excess acid in the oral cavity thus reducing the risk of acid erosion and dental caries, and to produce a tablet of the desired density and hardness.

In some aspects, the salt of carbonic acid (preferably sodium bicarbonate) is present in an amount of from 10 to 45 wt % based on the weight of the dental product, such as in an amount of from 10 to 40 wt. % based on the weight of the dental product, such as in an amount of from 10 to 35 wt. % based on the weight of the dental product, such as in an amount of from 10 to 30 wt. % based on the weight of the dental product, such as in an amount of from 10 to 25 wt. % of the dental product, such as in an amount of from 10 to 24 wt. % based on the weight of the dental product, such as in an amount of from 10 to 22 wt. % based on the weight of the dental product.

In some aspects, the salt of carbonic acid (preferably sodium bicarbonate) is present in an amount of from 10 to 30 wt % based on the weight of the dental product, such as in an amount of from 11 to 30 wt. % based on the weight of the dental product, such as in an amount of from 12 to 30 wt. % based on the weight of the dental product, such as in an amount of from 13 to 30 wt. % based on the weight of the dental product, such as in an amount of from 14 to 30 wt. % based on the weight of the dental product, such as in an amount of from 15 to 30 wt. % based on the weight of the dental product, such as in an amount of from 16 to 30 wt. % based on the weight of the dental product.

In one preferred aspect, the salt of carbonic acid (preferably sodium bicarbonate) is present in an amount of from 10 to 30 wt. % based on the weight of the dental product.

In one preferred aspect, the salt of carbonic acid (preferably sodium bicarbonate) is present in an amount of from 15 to 30 wt % based on the weight of the dental product.

In one preferred aspect, the salt of carbonic acid (preferably sodium bicarbonate) is present in an amount of from 15 to 25 wt % based on the weight of the dental product.

Sodium carbonate ($Na_2CO_3$) is a sodium salt of carbonic acid. It is also known as washing soda or soda ash. It has many industrial, food and cosmetic uses. Sodium bicarbonate ($NaHCO_3$) is also a sodium salt of carbonic acid. It is also known as sodium hydrogen carbonate, bicarbonate of soda, baking soda or nahcolite. It too has many industrial, food and cosmetic uses.

Acidifying Agent

The dental product of the present invention also comprises an acidifying agent. The acidifying agent according to the present invention comprises at least citric acid and malic acid, wherein the citric acid and malic acid are present in a weight ratio of from 4:1 to 1:1.

Citric acid is a weak organic acid with the chemical formula $C_6H_8O_7$. It is a natural preservative which is present in citrus fruits, and is used to add an acidic or sour taste to food or drinks. The chemical structure of citric acid is shown below:

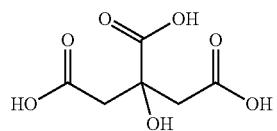 [SMILES: O=C(O)CC(O)(CC(=O)O)C(=O)O]

Malic acid is an organic acid with the chemical formula $C_4H_6O_5$. It is commonly used as a food additive. The chemical structure of malic acid is shown below:

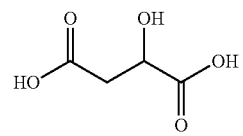

Without being bound by theory, citric and malic acid are potent salivary stimulants which increase the flow rate of saliva when placed in to the oral cavity. By stimulating salivary secretion the levels of calcium and phosphate ions present in the oral cavity are increased, due to the increased volume of saliva. Therefore this action supplements the concentration of available calcium and phosphate ions present in the oral cavity to aid the remineralisation of the tooth's enamel and dentin.

In some aspects, the acidifying agent is selected from citric acid, malic acid, tartaric acid, cream of tartar, lactic acid, ascorbic acid, acetic acid, fumaric acid, and mixtures thereof provided that the acidifying agent at least comprises citric acid and malic acid in a weight ratio of from 4:1 to 1:1.

In some aspects, the acidifying agent comprises citric acid and malic acid, together with a further acid or acids selected from organic acids. In some aspects, the acidifying agent comprises citric acid and malic acid, together with further acid or acids selected from tartaric acid, cream of tartar, lactic acid, ascorbic acid, acetic acid, fumaric acid, and mixtures thereof.

In one preferred aspect, the acidifying agent consists essentially of a mixture of citric acid and malic acid in a weight ratio of from 4:1 to 1:1.

In one preferred aspect, the acidifying agent consists of a mixture of citric acid and malic acid in a weight ratio of from 4:1 to 1:1.

In some aspects, the acidifying agent (preferably consisting of a mixture of citric acid and malic acid) is present in an amount of from 0.5 to 25 wt. % based on the weight of the dental product, such as in an amount of from 1 to 25 wt. % based on the weight of the dental product, such as in an amount of from 1.5 to 22.5 wt. % based on the weight of the dental product, such as in an amount of from 1.5 to 20 wt. % based on the weight of the dental product, such as in an amount of from 1.5 to 17.5 wt. % based on the weight of the dental product, such as in an amount of from 1.5 to 15 wt. % based on the weight of the dental product, such as in an amount of from 1.5 to 12.5 wt. % based on the weight of the dental product, such as in an amount of from 1.5 to 10 wt. % based on the weight of the dental product, such as in an amount of from 1.5 to 9 wt. % based on the weight of the dental product, such as in an amount of from 1.5 to 8 wt. % based on the weight of the dental product.

In some aspects, the acidifying agent (preferably consisting of a mixture of citric acid and malic acid) is present in an amount of from such as in an amount of from 1.5 to 22.5 wt. % based on the weight of the dental product, such as in an amount of from 2.5 to 17.5 wt. % based on the weight of the dental product, such as in an amount of from 3 to 15 wt. % based on the weight of the dental product, such as in an amount of from 3.5 to 12.5 wt. % based on the weight of the dental product, such as in an amount of from 4 to 10 wt. % based on the weight of the dental product, such as in an amount of from 4.5 to 10 wt. % based on the weight of the dental product, such as in an amount of from 5 to 10 wt. % based on the weight of the dental product, such as in an amount of from 5 to 9 wt. % based on the weight of the dental product, such as in an amount of from 5 to 8 wt. % based on the weight of the dental product.

In some aspects, the citric acid and malic acid are present in a weight ratio of from 4:1 to 1:1, such as in an amount of from 3.5:1 to 1:1, such as in an amount of from 3:1 to 1:1, such as in an amount of from 2.5:1 to 1:1, such as in an amount of from 2:1 to 1:1.

In some aspects, the citric acid and malic acid are present in a weight ratio of from 4:1 to 1.5:1, such as in an amount of from 4:1 to 2:1, such as in an amount of from 3.5:1 to 2:1, such as in an amount of from 3:1 to 2:1, such as in an amount of from 2.5:1 to 2:1.

In one preferred aspect, the citric acid and malic acid are present in a weight ratio of from 2.5:1 to 1.5:1.

In one preferred aspect, the citric acid and malic acid are present in a weight ratio of about 2:1.

In some aspects, the citric acid is present in an amount of from 1 to 15 wt. % based on the weight of the dental product, such as in an amount of from 1 to 12.5 wt. % based on the weight of the dental product, such as in an amount of from 1 to 10 wt. % based on the weight of the dental product, such as in an amount of from 1 to 7.5 wt. % based on the weight of the dental product.

In some aspects, the citric acid is present in an amount of from 1.5 to 15 wt. % based on the weight of the dental product, such as in an amount of from 2 to 15 wt. % based on the weight of the dental product, such as in an amount of from 2.5 to 15 wt. % based on the weight of the dental product, such as in an amount of from 3 to 15 wt. % based on the weight of the dental product, such as in an amount of from 3.5 to 15 wt. % based on the weight of the dental product.

In one preferred aspect, the citric acid is present in an amount of from 1 to 15 wt. % based on the weight of the dental product. In one preferred aspect, the citric acid is present in an amount of from 2 to 10 wt. % based on the weight of the dental product. In one preferred aspect, the citric acid is present in an amount of from 3.5 to 7.5 wt. % based on the weight of the dental product.

In some aspects, the malic acid is present in an amount of from 0.5 to 7.5 wt. % based on the weight of the dental product, such as in an amount of from 0.5 to 7 wt. % based on the weight of the dental product, such as in an amount of from 0.5 to 6.5 wt. % based on the weight of the dental product, such as in an amount of from 0.5 to 6 wt. % based on the weight of the dental product, such as in an amount of from 0.5 to 5.5 wt. % based on the weight of the dental product, such as in an amount of from 0.5 to 5 wt. % based on the weight of the dental product, such as in an amount of from 0.5 to 4.5 wt. % based on the weight of the dental product, such as in an amount of from 0.5 to 4 wt. % based on the weight of the dental product, such as in an amount of from 0.5 to 3.5 wt. % based on the weight of the dental product, such as in an amount of from 0.5 to 3 wt. % based on the weight of the dental product.

In some aspects, the malic acid is present in an amount of from 1 to 7.5 wt. % based on the weight of the dental product, such as in an amount of from 1.5 to 7.5 wt. % based on the weight of the dental product, such as in an amount of from 1.5 to 5 wt. % based on the weight of the dental product.

In one preferred aspect, the malic acid is present in an amount of from 1 to 5 wt. % based on the weight of the dental product.

Xylitol

The dental product of the present invention also comprises xylitol. Xylitol is a sugar alcohol also known as 1,2,3,4,5-pentahydroxypentane and xylite. Xylitol is commonly used as a sweetener.

As discussed herein, the addition of xylitol in the composition facilitates the remineralisation process and provides benefits due to its non-cariogenic properties. Remineralisation will naturally occur when the saliva is supersaturated with calcium and phosphate ions. However, agents can be added to oral care compositions to facilitate the remineralisation process. Xylitol has been shown to be particularly effective in oral care compositions, significantly due to its non-cariogenic properties and its ability to stimulate salivary secretion, but also because it has been shown to penetrate the sub-layers of enamel and dentin and facilitate the remineralisation process. Without wishing to be bound by theory, xylitol is thought to associate with calcium ions in aqueous solution and act as a calcium carrier, whilst simultaneously inhibiting the dissociation of calcium and phosphate ions from enamel. Therefore, the xylitol component of the present invention impairs plaque formation, boosts the levels of calcium and phosphate ions by stimulating salivary secretion, negates the effects of plaque acids and bacterial proliferation, whilst aiding the remineralisation of enamel and dentin.

The xylitol may be present in any suitable amount to achieve the desired aims of the present invention. In one aspect xylitol is present in an amount of no greater than 10 wt % based on the weight of the dental product, such as in an amount of no greater than 7.5 wt % based on the weight of the dental product, such as in an amount of no greater than 5 wt % based on the weight of the dental product, such as in an amount of no greater than 2.5 wt % based on the weight of the dental product, such as in an amount of no greater than 2 wt. % based on the weight of the dental product.

In one aspect xylitol is present in an amount of no less than 0.01 wt % based on the weight of the dental product, such as in an amount of no less than 0.1 wt % based on the weight of the dental product, such as in an amount of no less than 0.2 wt % based on the weight of the dental product, such as in an amount of no less than 0.3 wt % based on the weight of the dental product, such as in an amount of no less than 0.4 wt % based on the weight of the dental product.

In one aspect xylitol is present in an amount of from 0.1 to 10 wt % based on the weight of the dental product, such as in an amount of from 0.1 to 7.5 wt % based on the weight of the dental product, such as in an amount of from 0.1 to 5 wt % based on the weight of the dental product, such as in an amount of from 0.1 to 4 wt. % based on the weight of the dental product, such as in an amount of from 0.1 to 3 wt. % based on the weight of the dental product, such as in an amount of from 0.1 to 2.5 wt. % based on the weight of the dental product, such as in an amount of from 0.1 to 2 wt. % based on the weight of the dental product, such as in an amount of from 0.2 to 2 wt. % based on the weight of the dental product, such as in an amount of from 0.3 to 2 wt. % based on the weight of the dental product, such as in an amount of from 0.4 to 2 wt. % based on the weight of the dental product.

Composition Hardness

As discussed herein, we have found that the use of salts of carbonic acid, acidifying agents and other components results in compositions of varying hardness and that selection of the correct hardness is important for the experience of the user. The composition of the present invention confers a suitable hardness that means the composition does not readily fragment or fracture, and yet is not so hard as to cause harm to the user during use, for example by causing damage to the teeth.

In one aspect, the dental product of the present invention is provided in the form of a tablet which has a mean tablet breaking force of from 10 to 60N when tested in accordance with European Pharmacopoeia 2.9.8 "Resistance To Crushing Of Tablets". In one further aspect, the dental product of the present invention is provided in the form of a tablet which has a mean tablet breaking force of from 10 to 40N, such as from 10 to 30N, such as from 10 to 25N, such as from 15 to 25N, such as from 18 to 23N, when tested in accordance with European Pharmacopoeia 2.9.8 "Resistance To Crushing Of Tablets".

Thus in a further aspect the present invention provides a dental product in the form of a solid comprising
(a) a mineral source, wherein the mineral source comprises a source or sources of calcium ions, phosphate ions or both calcium ions and phosphate ions;
(b) a salt of carbonic acid;
(c) an acidifying agent; and
(d) xylitol;
wherein the dental product is provided in the form of a tablet which has a mean tablet breaking force of from 10 to 60N when tested in accordance with European Pharmacopoeia 2.9.8 "Resistance To Crushing Of Tablets". In one further embodiment of this aspect, the dental product of the present invention is provided in the form of a tablet which has a mean tablet breaking force of from 10 to 40N, such as from 10 to 30N, such as from 10 to 25N, such as from 15 to 25N, such as from 18 to 23N, when tested in accordance with European Pharmacopoeia 2.9.8 "Resistance To Crushing Of Tablets".

Preferred Compositions & Additional Components

The dental product of the present invention may also comprise one or more acceptable additives. The person skilled in the art is aware of a range of acceptable additives which are suitable for incorporation into such dental products. Fruit and herb extracts and juices, vegetable oils and essential oils are all compatible with the composition. Colours, both naturally derived and synthetic can be used to colour the dental product.

Essential oils possess well-known medicinal properties and have been shown to exhibit anti-microbial, antiseptic and astringent effects, in addition to inhibiting the formation of plaque and freshening the breath, when used in oral hygiene compositions. Active components of essential oils, such as menthol, thymol, eucalyptol, α/β-pinene and limonene, are present in many essential oils in varying concentrations.

Preferably the dental product of the present invention comprises aniseed oil, cardoman essential oil, cinnamon bark oil, clary sage essential oil, coriander seed oil, fennel essential oil, grapefruit essential oil, juniperberry oil, lavender oil, lemon oil, lime oil, neroli oil, orange oil, peppermint oil, rose oil, spearmint oil, basil oil, thyme oil, chamomile oil, sage oil, oregano oil and mixtures thereof.

In one aspect, the acceptable additives are selected from the group consisting of oils, flavourings, fragrances, colourings, edible lustres, fillers, binders, vitamins, and mixtures thereof.

In one preferred aspect, the dental product of the present invention further comprises one or more flavourings and one or more colourings.

In a preferred aspect, the dental product may further comprise precipitated silica as an acceptable additive. Precipitated silica is a silica ($SiO_2$) produced by precipitation from a solution containing silicate salts. It is generally used as a cleaning, thickening and polishing agent in toothpastes for oral health care.

In one aspect, the acceptable additives are present in amount of no greater than 10% by weight of the dental product. In one aspect, the acceptable additives are present in amount of no greater than 9% by weight of the dental product. In one aspect, the acceptable additives are present in amount of no greater than 8% by weight of the dental product. In one aspect, the acceptable additives are present in amount of no greater than 7% by weight of the dental product. In one aspect, the acceptable additives are present in amount of no greater than 6% by weight of the dental product. In one aspect, the acceptable additives are present in an amount of no greater than 5% by weight of the dental product.

In one preferred aspect, the acceptable additives are present in an amount of from 0.01 to 10 wt. % based on the weight of the dental product, such as in an amount of from 0.01 to 7.5 wt. % based on the weight of the dental product.

In some preferred aspects, the dental product of the present invention comprises an outer coating. In one preferred aspect, the dental product is a solid tablet that is coated with an outer coating material. In one preferred aspect, the coating comprises at least the following components:
(a) a mineral source, wherein the mineral source comprises a source or sources of calcium ions, phosphate ions or both calcium ions and phosphate ions;
(b) a salt of carbonic acid; and
(c) an acidifying agent.

In a preferred aspect, the dental product is a mouthwash. In a preferred aspect, the dental product is provided in the form of a solid tablet for use as a mouthwash.

In a preferred aspect, the dental product comprises
(a) a mineral source (wherein the mineral source comprises a source or sources of calcium ions and/or phosphate ions) in an amount of from 40 to 60 wt % based on the weight of the dental product;
(b) a salt of a carbonic acid in an amount of from 10 to 45 wt % based on the weight of the dental product;
(c) an acidifying agent in an amount of from 1.5 to 22.5 wt % based on the weight of the dental product; and
(d) xylitol in an amount of from 0.1 to 10 wt % based on the weight of the dental product, wherein the acidifying agent comprises at least citric acid and malic acid, wherein the citric acid and malic acid are present in a weight ratio of from 4:1 to 1:1.

The weight ratio of the salt of carbonic acid to the acidifying agent may be sufficient to ensure complete neutralisation of the acid during use. In a preferred aspect, the salt of a carbonic acid and the acidifying agent are present in a weight ratio of at least 2:1, such as in a weight ratio of from 10:1 to 2:1, such as from 8:1 to 2:1, such as from 7:1 to 2:1, such as from 6:1 to 2:1, such as from 5:1 to 2:1.

The above ranges provide preferred amounts of each of the components. Each of these ranges may be taken alone or combined with one or more other component ranges to provide a preferred aspect of the invention.

Process

In another aspect, there is provided process for the production of a dental product comprising the steps of:
i) preparing a composition comprising
  (a) a mineral source, wherein the mineral source comprises a source or sources of calcium ions, phosphate ions or both calcium ions and phosphate ions;
  (b) a salt of carbonic acid;
  (c) an acidifying agent; and
  (d) xylitol,
  wherein the acidifying agent comprises at least citric acid and malic acid, wherein the citric acid and malic acid are present in a weight ratio of from 4:1 to 1:1; and ii) pressing the composition of step i) into the form of a tablet.

The shape of the dental products of the present invention is not limited provided that it is in a size capable of being placed in the mouth of a user. It may be that tablets of the dental products are provided with a shape which would be aesthetically pleasing and/or which aids in the use of the product.

Therefore, in one aspect of the process of the present invention, the mixture of step i) is caused to solidify in a predetermined shape.

In one aspect of the process of the present invention, the mixture of step i) is pressed into a mould, allowed to solidify, and then turned out to produce the dental product.

As described herein, the dental product may further comprise one or more acceptable additives. In one aspect, the process further comprises the step of combining with the mixture of step i) one or more acceptable additives as defined above.

Method

In one aspect of the present invention, there is provided a method for cleansing the mouth and freshening breath, the method comprising:
(i) dissolving in the mouth a dental product as defined herein;
(ii) rinsing the dissolved product from the mouth.

In one preferred aspect, the dental product is dissolved in the mouth by placing the dental product on the tongue of the user.

EXAMPLES

The invention will now be described with reference to the following non-limiting examples.

Example 1

A dental product having the following composition was prepared.
The Formulation for the composition will be as follows;

| Phase | Raw Material | wt. % |
|---|---|---|
| A | Sodium Bicarbonate | 16.52 |
|  | Dicalcium Phosphate | 54.33 |
|  | Precipitated Silica | 12.80 |
|  | Turmeric Powder | 3.15 |
|  | Xylitol | 0.65 |
|  | Sorbitol | 3.75 |
|  | Citric Acid | 5.10 |

| Phase | Raw Material | wt. % |
|---|---|---|
| B | Malic Acid | 2.55 |
|  | Peppermint Oil | 1.15 |

The dental product having the above composition was formulated as follows:
1. Weigh out and sieve all component parts of phase A.
2. Homogenise the resulting free-flowing powders and place into a pre-heated oven for 30 minutes at 80 degrees centigrade.
3. Incorporate the component parts of phase B into phase A and mix thoroughly.
4. Feed the resulting free-flowing powder into a tablet press and compress the powder to create a tablet of the desired hardness.

When used the product was found to have a rate of effervescent that was sufficient to liberate organic particulates from between the teeth and around the gum line and reduce or prevent accumulation of plaque, whilst the flavour was not adversely affected by the concentration of citric acid present.

Example 2

A dental product having the following composition was prepared.
The Formulation for the composition was as follows:

| Phase | Raw Material | wt. % |
|---|---|---|
| A | Sodium Bicarbonate | 21.27 |
|  | Dicalcium Phosphate | 45.21 |
|  | Precipitated Silica | 12.81 |
|  | Spirulina Powder | 3.73 |
|  | Sea Salt Fine | 5.91 |
|  | Xylitol | 0.45 |
|  | Sorbitol | 2.30 |
|  | Citric Acid | 3.38 |
| B | Malic Acid | 1.69 |
| C | Sodium Bicarbonate | 0.53 |
|  | Dicalcium Phosphate | 1.29 |
|  | Precipitated Silica | 0.36 |
|  | Spirulina Powder | 0.06 |
|  | Sea Salt Fine | 0.09 |
| D | Citric Acid | 0.12 |
|  | Malic Acid | 0.06 |
| E | Thyme Oil | 0.75 |

The dental product having the above composition was formulated as follows:
1. Weigh out and sieve all component parts of phase A.
2. Homogenise the resulting free-flowing powders and place into a pre-heated oven for 30 minutes at 80 degrees centigrade.
3. Incorporate the component parts of phase B into phase A and mix thoroughly.
4. Feed the resulting free-flowing powder into a tablet press and compress the powder to create a tablet of the desired hardness.
5. Sieve and homogenise the component parts of phase C.
6. Incorporate the component parts of phase D into phase C and mix thoroughly.
7. Spray the tablet of phases A & B with the oil of phase E and coat the tablet with the free-flowing powder of phases C & D.
8. Allow to dry at room temperature for 2 hours.

When used the product was found to have a rate of effervescent that was sufficient to liberate organic particulates from between the teeth and around the gum line and reduce or prevent accumulation of plaque, whilst the flavour was not adversely affected by the concentration of citric acid present.

Example 3 (Not in Acordance with the Invention)

Dental products having the following compositions were formulated as follows:
1. Weigh out and sieve all component parts of phase A.
2. Homogenise the resulting free-flowing powders and place into a pre-heated oven for 30 minutes at 80 degrees centigrade.
3. Incorporate the component parts of phase B into phase A and mix thoroughly.
4. Feed the resulting free-flowing powder into a tablet press and compress the powder to create a tablet of the desired hardness.
5. Allow to dry at room temperature for 2 hours.

Sample 3.1

| Phase | Raw Material | wt % |
|---|---|---|
| A | Sodium Bicarbonate | 21.25 |
|   | Dicalcium Phosphate | 44.60 |
|   | Menthol Crystals | 2.90 |
|   | Precipitated Silica | 11.55 |
|   | Xylitol | 1.50 |
|   | FD&C Colour Solution (10%) | 0.40 |
|   | Flavour | 10.80 |
| B | Citric Acid | 7.00 |
| Total | | 100 |

Effervescence of this sample was far too vigorous and adversely effected the taste of the overall composition to the point that is was unpalatable. It was also deemed to be a sensitising agent, causing the gums and gum line to become sensitive.

Sample 3.2

| Phase | Raw Material | wt % |
|---|---|---|
| A | Sodium Bicarbonate | 21.25 |
|   | Dicalcium Phosphate | 44.60 |
|   | Menthol Crystals | 2.90 |
|   | Precipitated Silica | 11.55 |
|   | Xylitol | 1.50 |
|   | FD&C Colour Solution (10%) | 0.40 |
|   | Flavour | 10.80 |
| B | Tartaric Acid | 7.00 |
| Total | | 100 |

The like for like replacement of citric acid with tartaric acid yielded a minimally effervescent composition. The rate of dissolution was very slow, although the tablet did completely dissolve. The sample was found to provide a very unpleasant taste Sample 3.3

| Phase | Raw Material | wt % |
|---|---|---|
| A | Sodium Bicarbonate | 21.25 |
|   | Dicalcium Phosphate | 44.60 |
|   | Menthol Crystals | 2.90 |
|   | Precipitated Silica | 11.55 |
|   | Xylitol | 1.50 |
|   | FD&C Colour Solution (10%) | 0.40 |
|   | Flavour | 10.80 |
| B | Malic Acid | 7.00 |
| Total | | 100 |

Malic acid is known in the art to be an alternative organic acid due to its flavour enhancing properties. However, this sample tablet simply dissolved in the mouth without any effervescent action.

Sample 3.4

| Phase | Raw Material | wt % |
|---|---|---|
| A | Sodium Bicarbonate | 21.25 |
|   | Dicalcium Phosphate | 44.60 |
|   | Menthol Crystals | 2.90 |
|   | Precipitated Silica | 11.55 |
|   | Xylitol | 1.50 |
|   | FD&C Colour Solution (10%) | 0.40 |
|   | Flavour | 10.80 |
| B | Citric Acid | 2.33 |
|   | Malic Acid | 4.67 |
| Total | | 100 |

This sample contained a blend of citric acid and malic acid in a ratio of 1:2. The sample was found to suffer from the same disadvantages sample 3.3, namely poor effervescence.

Example 4

Tablets prepared in accordance with Example 1 and Example 2 were tested in accordance with European Pharmacopoeia 2.9.8 "Resistance To Crushing Of Tablets". The test was performed as follows:

Apparatus—The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 newton. The current testing was performed using a 'Dr Schleuniger Pharmatron 5Y Hardness Tester'. The tablets were tested with their sides flush against the tester 'jaws'.

Operating Procedure—Place the tablet between the jaws, taking into accounts, where applicable, the shape, the breakmark and the inscription; for each measurement orient the tablet in the same way with respect to the direction of application of the force. Carry out the measurement on 10 tablets, taking care that all fragments of tablets have been removed before each determination.

Expression Of Results—results were expressed as the mean value of the forces measured, expressed in Newtons.

Results

| Sample | Mean tablet breaking force (N) |
|---|---|
| Example 1 | 22.9 |
| Example 2 | 18.6 |

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A dental product in the form of a solid comprising:
   (a) a mineral source, wherein the mineral source comprises a source or sources of calcium ions, phosphate ions or both calcium ions and phosphate ions;
   (b) a salt of carbonic acid;
   (c) an acidifying agent; and
   (d) xylitol;
   wherein the acidifying agent comprises at least citric acid and malic acid, wherein the citric acid and malic acid are present in a weight ratio of from 4:1 to 1.5:1.

2. A dental product according to claim 1 wherein the mineral source comprises a source or sources of calcium ions and phosphate ions.

3. A dental product according to claim 1 wherein the mineral source is selected from amorphous calcium phosphate, casein phosphor-peptides-amorphous calcium phosphate, monocalcium phosphate, dicalcium phosphate, tricalcium phosphate, octacalcium phosphate, calcium carbonate and mixtures thereof.

4. A dental product according to claim 1, wherein the mineral source comprises at least dicalcium phosphate.

5. A dental product according to claim 1, wherein the mineral source is present in an amount of from 40 to 60 wt % based on the weight of the dental product.

6. A dental product according to claim 1, wherein the mineral source is present in an amount of from 45 to 55 wt % based on the weight of the dental product.

7. A dental product according to claim 1, wherein the salt of carbonic acid is selected from alkali metal carbonates and mixtures thereof.

8. A dental product according to claim 1, wherein the salt of carbonic acid comprises at least sodium bicarbonate.

9. A dental product according to claim 1, wherein the salt of carbonic acid is present in an amount of from 10 to 45 wt % based on the weight of the dental product.

10. A dental product according to claim 1, wherein the salt of carbonic acid is present in an amount of from 10 to 30 wt % based on the weight of the dental product.

11. A dental product according to claim 1, wherein the acidifying agent further comprises an acid selected from the group consisting of tartaric acid, cream of tartar, lactic acid, ascorbic acid, acetic acid, fumaric acid and mixtures thereof.

12. A dental product according to claim 1, wherein the acidifying agent consists of a mixture of citric acid and malic acid.

13. A dental product according to claim 1, wherein the acidifying agent is present in an amount of from 1.5 to 22.5 wt % based on the weight of the dental product.

14. A dental product according to claim 1, wherein the acidifying agent is present in an amount of from 1.5 to 10 wt % based on the weight of the dental product.

15. A dental product according to claim 1, wherein the acidifying agent comprises citric acid and malic acid in a weight ratio of from 3:1 to 1.5:1.

16. A dental product according to claim 1, wherein the acidifying agent comprises citric acid and malic acid in a weight ratio of from 2.5:1 to 1.5:1.

17. A dental product according to claim 1, wherein citric acid is present in an amount of from 1 to 15 wt % based on the weight of the dental product.

18. A dental product according to claim 1, wherein citric acid is present in an amount of from 2 to 10 wt % based on the weight of the dental product.

19. A dental product according to claim 1, wherein malic acid is present in an amount of from 0.5 to 7.5 wt % based on the weight of the dental product.

20. A dental product according to claim 1, wherein malic acid is present in an amount of from 1 to 5 wt % based on the weight of the dental product.

21. A dental product according to claim 1, wherein the xylitol is present in an amount of from 0.1 to 10 wt % based on the weight of the dental product.

22. A dental product according to claim 1, wherein the xylitol is present in an amount of from 0.1 to 2 wt % based on the weight of the dental product.

23. A dental product according to claim 1, further comprising one or more additives selected from the group consisting of oils, flavourings, colourings, edible lustres, fillers, binders, vitamins, and mixtures thereof.

24. A dental product according to claim 23 further comprising one or more flavourings and one or more colourings; and one or more additives selected from the group consisting of oils, edible lustres, fillers, binders, vitamins, and mixtures thereof.

25. A dental product according to claim 1, wherein the dental product is a mouthwash.

26. A process for the production of a dental product as defined in claim 1, comprising the steps of:
   i) preparing a composition comprising:
      (a) a mineral source, wherein the mineral source comprises a source or sources of calcium ions, phosphate ions or both calcium ions and phosphate ions;
      (b) a salt of carbonic acid;
      (c) an acidifying agent; and
      (d) xylitol;
         wherein the acidifying agent comprises at least citric acid and malic acid, wherein the citric acid and malic acid are present in a weight ratio of from 4:1 to 1.5:1; and
   ii) pressing the composition of step i) into the form of a tablet.

27. A method for cleansing the mouth and freshening the breath, the method comprising:
   dissolving in the mouth a dental product as defined in claim 1;
   (ii) rinsing the dissolved product from the mouth.

* * * * *